Feb. 14, 1961 E. S. BOERNER Plant Pat. 2,025
CHRYSANTHEMUM PLANT
Filed May 20, 1960
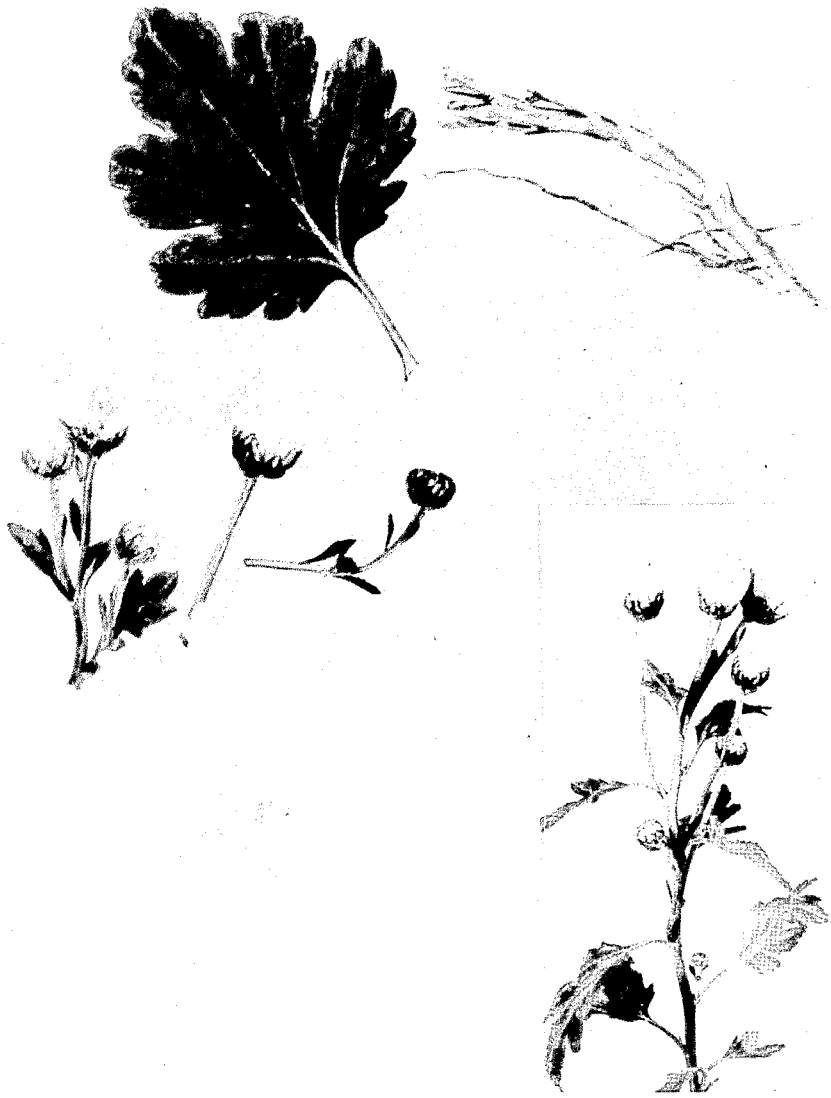
Inventor.
E. S. Boerner
By: Robb & Robb
Attorneys.

United States Patent Office

Plant Pat. 2,025
Patented Feb. 14, 1961

2,025

CHRYSANTHEMUM PLANT

Eugene S. Boerner, Newark, N.Y., assignor to Jackson & Perkins Company, Newark, N.Y., a corporation of New York Filed May 20, 1960, Ser. No. 30,695

1 Claim. (Cl. 47—60)

The present invention relates to a new and distinct variety of chrysanthemum plant of the shaggy decorative class, which was originated by me by crossing an unnamed and unpatented seedling derived from a cross of "Cockatoo" (Plant Patent No. 1,171)×an unnamed and unpatented large-flowered golden-colored Hortorum seedling with the variety "Seagull" (Plant Patent No. 1,130).

The primary objective of this breeding was to produce a new chrysanthemum variety which combines the large flower size that is characteristic of the unnamed seedling parent, with the earliness and White flower color as are characteristic of the parent variety "Seagull." This objective was fully achieved along with other desirable improvements, as evidenced by the following characteristics which are outstanding in the new variety and which distinguish it from its parents, as well as from all other varieties of which I am aware:

(1) A branching plant habit;

(2) A distinctive Dark Cress Green color of the foliage;

(3) Earliness of bloom;

(4) Large flower size; and (5) A distinctive White general color tonality of the flowers, with the lower half of the flower petals very lightly overcast with Barium Yellow color.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, near mid-morning during the first part of the month of October:

Parentage: Seedling.

*Seed parent.*—An unnamed seedling of "Cockatoo"×an unnamed large-flowered golden-colored Hortorum seedling.

*Pollen parent.*—"Seagull."

Classification: Shaggy decorative.

Growth: Free.

Cold resistance: Hardy.

Blooming period: From about the end of September to frost.

*Flower*

Bud:

*Color.*—When sepals first divide—Mustard Yellow, Plate 16. When petals begin to unfurl—White, Plate 53, lightly overcast with Empire Yellow, Plate 4. When half-blown: inside of petals—White, Plate 53, lightly overcast with Amber Yellow, Plate 16; outside of petals—White, Plate 53, lightly overcast with Buff-Yellow, Plate 4.

*Peduncle.*—Color—Light Hellebore Green, Plate 17. Strength—strong.

Bloom:

*Size.*—5 inches.

*Stem.*—Strong.

*Form.*—Shaggy decorative.

*Petalage.*—Double; stamens are fully exposed when the flower is fully open.

*Color.*—Center of flower—Pinard Yellow, Plate 4. Outer petals—White, Plate 53. Base of petals—Green-Yellow, Plate 5. Inside of petals—White, Plate 53, with lower half of petals very lightly overcast with Barium Yellow, Plate 16. Reverse of petals—White, Plate 53, lightly overcast with Pale Chalcedony Yellow, Plate 17.

*Petals.*—Texture—thick. Form—oval.

*Fragrance.*—Characteristic chrysanthemum.

*Plant*

Form: Upright; branching from crown.

Growth: Free.

Foliage:

*Size.*—Medium.

*Quantity.*—Normal.

*Color.*—Upper side—Dark Cress Green, Plate 31. Reverse side—Bice Green, Plate 17.

*Texture.*—Leathery.

I claim:

A new and distinct variety of chrysanthemum plant of the shaggy decorative class, substantially as herein shown and described, characterized particularly as to novelty by the unique combination of a branching habit of growth, Dark Cress Green color of the foliage, an early blooming habit, large flower size, and a distinctive White general color tonality of the flowers, with the lower half of the flower petals very lightly overcast with Barium Yellow color.

No references cited.